US00RE44007E

(19) United States
(12) Reissued Patent
Ferrieu

(10) Patent Number: US RE44,007 E
(45) Date of Reissued Patent: Feb. 19, 2013

(54) LOW-NOISE SPECTROSCOPIC ELLIPSOMETER

(75) Inventor: Frederic Ferrieu, Meylan (FR)

(73) Assignee: Fahrenheit Thermoscope LLC, Las Vegas, NV (US)

(21) Appl. No.: 11/520,061

(22) Filed: Sep. 12, 2006

Related U.S. Patent Documents

Reissue of:
(64) Patent No.: 6,791,684
Issued: Sep. 14, 2004
Appl. No.: 10/168,041
PCT Filed: Jun. 8, 2001
PCT No.: PCT/FR01/01781
§ 371 (c)(1),
(2), (4) Date: Jun. 13, 2002
PCT Pub. No.: WO01/94898
PCT Pub. Date: Dec. 13, 2001

(30) Foreign Application Priority Data

Jun. 9, 2000 (FR) ..... 00 07425

(51) Int. Cl.
*G01J 3/28* (2006.01)

(52) U.S. Cl. ..... 356/326; 356/451; 356/317; 250/225; 250/576; 315/292

(58) Field of Classification Search ..... 356/365, 356/369, 370, 316–320, 322, 326, 338, 451–453; 250/225, 576, 370.15, 371, 352, 397, 372, 250/390.1; 315/292, 360, 362
See application file for complete search history.

(56) References Cited

U.S. PATENT DOCUMENTS 4,284,351 A 8/1981 Alldritt et al.
4,622,485 A 11/1986 Miyashita et al.
4,822,168 A 4/1989 Nogami et al.
5,020,015 A 5/1991 Jones et al.
5,298,973 A 3/1994 Fukazawa et al.
5,313,044 A * 5/1994 Massoud et al. ..... 219/121.85
5,329,357 A 7/1994 Bernoux et al.
5,386,121 A 1/1995 Barbee et al.
5,657,126 A 8/1997 Ducharme et al.
5,757,671 A 5/1998 Drevillon et al.
5,956,144 A 9/1999 Kaplan et al.
6,125,687 A * 10/2000 McClelland et al. ..... 73/19.01
6,134,011 A 10/2000 Klein et al.
6,307,627 B1 10/2001 Vurens (Continued)

FOREIGN PATENT DOCUMENTS

DE 29521772 8/1998
DE 29521772 9/1998

(Continued)

OTHER PUBLICATIONS

European Application 01945381.0; Filed Jun. 8, 2001; 18 pages.

(Continued)

*Primary Examiner* — Haiss Philogene

(57) ABSTRACT

A spectroscopic ellipsometer comprising a light source (1) emitting a light beam, a polarizer (2) placed on the path of the light beam emitted by the light source, a sample support (9) receiving the light beam output from the polarizer, a polarization analyzer (3) for passing the beam reflected by the sample to be analyzed, a detection assembly which receives the beam from the analyzer and which comprises a monochromator (5) and a photodetector (4), and signal processor means (6) for processing the signal output from said detection assembly, and including counting electronics (13). Cooling means (12) keep the detection assembly at a temperature below ambient temperature, thereby minimizing detector noise so as to remain permanently under minimum photon noise conditions. It is shown that the optimum condition for ellipsometric measurement is obtained by minimizing all of the sources of noise (lamps, detection, ambient).

31 Claims, 3 Drawing Sheets

U.S. PATENT DOCUMENTS

| | | | | |
|---|---|---|---|---|
| 6,415,078 | B1 | 7/2002 | Shigehara et al. | |
| 6,485,703 | B1 * | 11/2002 | Cote et al. | 424/9.1 |
| 6,515,744 | B2 | 2/2003 | Wei | |
| 6,535,286 | B1 * | 3/2003 | Green et al. | 356/369 |
| 6,600,560 | B2 | 7/2003 | Mikkelsen et al. | |
| 6,633,831 | B2 * | 10/2003 | Nikoonahad et al. | 702/155 |

FOREIGN PATENT DOCUMENTS

| | | |
|---|---|---|
| DE | 19721045 | 11/1998 |
| JP | 62-266439 | 11/1987 |
| JP | 63-308543 | 12/1988 |
| JP | 07-239298 | 9/1995 |
| JP | 08-166345 | 6/1996 |
| JP | 09-079905 | 3/1997 |
| JP | 9079905 | 3/1997 |
| JP | 09079905 | 7/1997 |
| JP | 10-501072 | 1/1998 |
| JP | 10-281992 | 10/1998 |
| JP | 11-508033 | 7/1999 |

OTHER PUBLICATIONS

Communication from the European Patent Office Under EPC Article 96(2); European Application 01945381.0; Sep. 29, 2003; 13 pages.
Response to Communication Dated Sep. 29, 2003; European Application 01945381.0; Apr. 1, 2004; 7 pages.
Communication from the European Patent Office Under EPC Article 96(2); European Application 01945381.0; Jul. 22, 2004; 6 pages.
Response to Communication Dated Jul. 22, 2004; European Application 01945381.0; Jan. 27, 2005; 5 pages.
Communication from the European Patent Office Under EPC Article 96(2); European Application 01945381.0; Jul. 1, 2005; 3 pages.
Response to Communication Dated Jul. 1, 2005; European Application 01945381.0; Oct. 27, 2005; 7 pages.
Communication from the European Patent Office Under EPC Article 96(2); European Application 01945381.0; Jan. 31, 2007; 3 pages.
Communication Dated May 30, 2007; European Application 01945381.0; 5 pages.
French Preliminary Search Report for Application FR 0007425; search completed Feb. 19, 2001; 3 pages.
International Preliminary Examination Report for Application PCT/FR01/01781; search completed Jun. 19, 2002; 11 pages.
International Search Report for application PCT/FR01/01781; search completed on Oct. 10, 2001; 6 pages.
Concise Explanation of Non-English Language Documents Under 37 C.F.R. § 1.98(a)(3); NPL References 1-9; U.S. Appl. No. 11/520,061; Filed with Information Disclosure Statement on Sep. 4, 2008.
Collins, et al., "Dual Rotating Compensator Multichannel Ellipsometer: Instrument Design for Real-time Mueller Matrix Spectroscopy of Surfaces and Films". Pennsylvania State University, Published Aug. 1999.
Azzam, et al., "Ellipsometry and Polarized Light", Elsevier Science Publishing Co.; B.V.1977, ISBNO-7204-0694-3, 3 pages.
Hamamatsu, " Model C1050-01 Photon Counting Unit", Instruction Manual, Hamamatsu Photonics kk/Electron Tubes Div. 1988, 11 pages.
Hamamatsu, "Accessories for Photo Multiplier Tubes", Hamamatsu Photonics kk/Electron Tubes Div., May 5, 1991, 2 pages.
J.A. Woollam Co., Operators Manual, Variable Angle of Incidence Spectroscopic Ellipsometry (VASE), 10 pages, Jun. 1989.
Official Action in Japanese Application No. 2002-502401 issued Sep. 28, 2010, 3 pages. English Translation Available.
Office Action in Japanese Patent Application No. 2002-502401 issued Sep. 2, 2011, 8 pages.
Office Action in JP Application No. 2002-502401 mailed Jun. 8, 2012, 2 pages.
Hamamatsu model C1050-01 photon counting unit.*
Hamamatsu, "Accessories for photomultiplier tubes".*
Variable angle of incidence spectroscopic ellipsometry (VASE).*
Azzam et al., "Ellipsometry and polarized light".*

* cited by examiner

LOW-NOISE SPECTROSCOPIC ELLIPSOMETER

Matter enclosed in heavy brackets [ ] appears in the original patent but forms no part of this reissue specification; matter printed in italics indicates the additions made by reissue.

This is a non-provisional application claiming the benefit of International application number PCT/FR01/01781 filed Jun. 8, 2001.

GENERAL FIELD AND STATE OF THE ART

Background

The principles of a known state of the art ellipsometer are shown in FIG. 1.

Such an ellipsometer conventionally comprises a light source 1, a polarizer 2, an analyzer 3, and a detector 4 associated with a monochromator 5.

Those various elements are placed in such a manner that light output by the source 1 passes thorough the polarizer 2 before reaching a sample E to be analyzed, and then after being reflected on the sample E, it passes through the analyzer 3 prior to reaching the detector 4 after passing through the monochromator 5 which is generally a photomultiplier.

One of the two elements constituted by the polarizer 2 and the analyzer 3 is a rotary element.

The output from the detector 4 is connected to processor means 6 which perform Fourier analysis on the modulated signal as measured by the detector 4 in order to determine information relating to the surface state of the sample E.

It is recalled that when light is reflected on a sample E, its polarization is modified and that an ellipsometer setup makes it possible to measure firstly the phase difference $\Delta$ and secondly the ratio tan ($\Psi$) between the parallel and perpendicular polarization components of the beam as reflected on the sample.

By means of the monochromator 5, it is possible to perform measurements at different wavelengths, thereby characterizing the optical properties of the material.

For a general presentation of spectroscopic ellipsometric techniques, reference can advantageously be made to U.S. Pat. No. 5,329,357 (Bernoux et al.) which relates specifically to the advantage of adding optical fibers to the setup.

The visible spectroscopic ellipsometers available on the market generally operate in a spectral range of 1 micrometer (μm) to 230 nanometers (nm), using a xenon arc source (selected for high radiant flux density or "irradiance").

Nevertheless, ellipsometers have been proposed that are capable of operating over a broader spectral range than the above-mentioned ellipsometers and that include an additional source, such as a deuterium ($D_2$) source that provides less of a point source, emitting in the range 130 nm to 700 nm at a power of 30 watts (W) to a few hundreds of watts or more.

The detectors that are used are generally detectors of the Si or Ge photodiode type or photomultipliers (generally multi-alkali photomultipliers), operating at ambient temperature.

They use very high quality optical systems, possessing polarization extinction coefficients of about $10^{-5}$, and very high transparency, even in the ultraviolet.

This makes it possible in the above-specified spectral range to determine the $\Psi$ and $\Delta$ coefficients with precision equal to or less than $1/1000^{th}$ of a degree (°).

Furthermore, the processor means of most ellipsometers implement a simplified photon counting method, which method is known as the "Hadamard method". That method consists in counting photons with a signal that is amplitude sampled over a very limited number of channels: eight counters or channels, for each period of rotation of the rotary element of the ellipsometer (a configuration with a rotary polarizer or analyzer (modulated polarization) and/or a rotating plate (phase modulation)).

Drawbacks of State of the Art Ellipsometers

Ellipsometers of the type described above present several limitations.

A first limitation is associated directly with fluctuations in the source, i.e. with its lack of stability, with this constraint being known as shot noise limitation (SNL).

Another limitation is associated with noise coming from ambient light and also referred to as "leakage noise", which can in theory be eliminated by isolating the entire ellipsometer (and not only the photomultiplier) completely from ambient light, but which nevertheless remains a difficulty encountered by many ellipsometer manufacturers.

Another limitation lies in the dark current or intrinsic noise associated with the photomultiplier and its internal amplification system. This noise is commonly referred to as detector noise limitation (DNL). It should be observed that all of the frequencies corresponding to the bandwidth of the photomultiplier are generally present therein.

Thus, the Hadamard sums (as determined over quarter periods of the modulated signal) are calculated by taking account of a previously measured offset which corresponds to the leakage noise and to the DNL.

Nevertheless, although conventional ellipsometers correspond in practice to synchronous detection (in-phase frequency filtering of the signal modulation), the Hadamart method becomes difficult when the amplitude of the modulation is low.

For a signal modulated at $\Omega$, the amplitude of the spectrum component at $2\Omega$ in the signal is of the same order of magnitude as the amplitude of the noise (with this being true more particularly in the ultraviolet where counts of only 100 to 1000 counts per second (cps) are measured).

The signal components are thus "buried" in the noise level which itself corresponds to a superposition of the spectrum density of the source noise, shot noise when using a xenon arc, ambient light, and noise from the detector and its associated electronics.

Furthermore, with conventional ellipsometers, when it is desired to work at wavelengths shorter than 200 nm, the observed signal/noise ratio is unfavorable.

The only known way of eliminating the effects of the various sources of noise is to increase acquisition times.

Unfortunately, measurement is then subject to systematic error, in particular concerning wavelengths shorter than 200 nm. This means that equipment must be pre-calibrated in use.

Furthermore, it should also be observed that another problem encountered with ellipsometers that use additional sources to enlarge their operating range is the problem of their cost and of the power that must be supplied to them.

Under such conditions, it is practically impossible to envisage a system that is sufficiently compact for in situ measurement (integrated metrology) even in a photon-counting system as described above. The impossibility of having a measurement head internal to the metrological casing leads to a limitation due to the windows of the casing giving rise to birefringent effects that need to be corrected.

SUMMARY OF THE INVENTION

An object of the invention is to mitigate those drawbacks.

In particular, the invention provides an ellipsometer structure in which noise is minimized.

Techniques are known, in particular from the abstract of Japanese patent application No. 0907995, that consist in cooling photomultipliers in applications that are very different from ellipsometer applications.

Those cooling techniques are not intended in any way to reduce noise. They serve to lower detection limits as much as possible.

The invention proposes a spectroscopic ellipsometer comprising a light source emitting a light beam, a polarizer placed on the path of the light beam emitted by the light is source, a sample support receiving the light beam output from the polarizer, a polarization analyzer for passing the beam reflected by the sample to be analyzed, a detection assembly which receives the beam from the analyzer and which comprises a monochromator and a photodetector, and signal processor means for processing the signal output from said detection assembly, and including counting electronics.

This ellipsometer presents the characteristic of comprising cooling means for keeping the detection assembly at a temperature lower than ambient temperature, in particular at a temperature of about −15° C., or lower.

Also advantageously, its source is a deuterium lamp preferably having a power of about 30 watts.

Other low noise sources can be envisaged, and in particular plasma lamp and halogen lamp sources.

Also advantageously, the counting electronics is suitable for performing amplitude sampling over a number of channels lying in the range 8 (Hadamard equivalent) up to 1024 (filtered Fourier), and particularly preferably about 1000 or more, in particular a number of channels lying in the range 1024 to 8192 (depending on the type of encoder).

The processing means implement Fourier analysis on the signals sampled in this way.

Thus, the proposed ellipsometer enables noise to be minimized (to improve its precision): i) with total protection from ambient light; ii) no polluting environment (mechanical vibration and/or sources of electromagnetic noise); and a detector operating by counting photons in a minimum intrinsic noise level which is obtained in this case by cooling (12) to keep the detection assembly at a temperature lower than ambient temperature. By providing better performance in terms of signal detection, it makes it possible to use optical fibers all the way to 160 nm. This makes it possible to operate in compact manner in the context of integrated metrology associated with current development of cluster tools in the field of thin layer technology. The system becomes fully integrated in the in situ casing since it makes it possible to use films.

BRIEF DESCRIPTION OF THE FIGURES

Other characteristics and advantages of the invention appear further from the following description which is purely illustrative and non-limiting and should be read with reference to the accompanying drawings, in which.

DESCRIPTION OF POSSIBLE EMBODIMENTS OF THE INVENTION

Background

Figure 1:
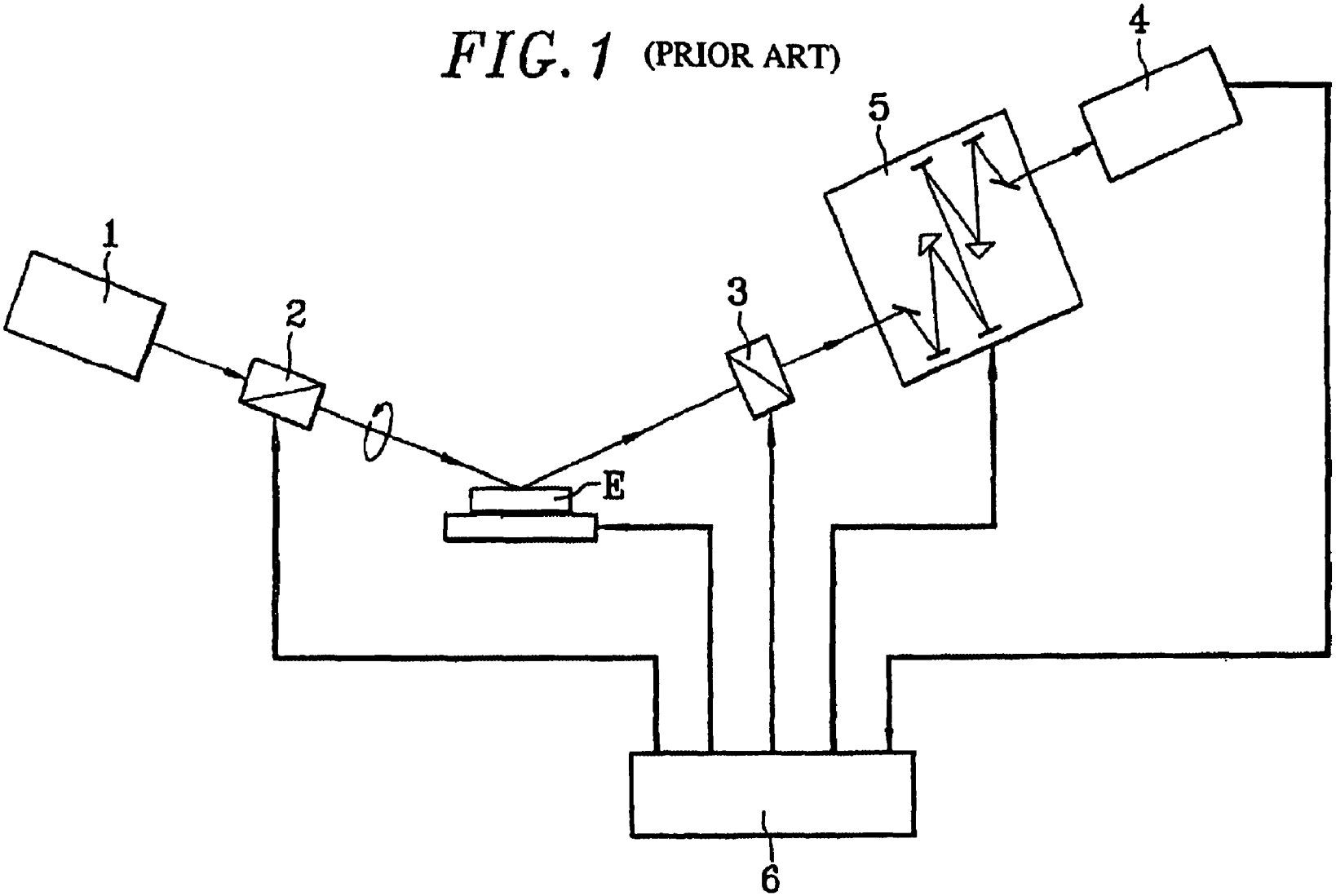
FIG. 1 (PRIOR ART)
FIG. 1, described above, is a diagram illustrating the principles of a spectroscopic ellipsometer known in the state of the art.

A spectroscopic ellipsometer constituting a possible embodiment of the invention presents the following characteristics.

1) Its source 1 is a low noise source, i.e. a source whose frequency dispersion is much less than that of a xenon arc lamp.

Such a source is advantageously a deuterium $D_2$ lamp.

Deuterium $D_2$ lamps are lamps having particularly low noise. They are much more stable than xenon arc lamps (stability in a ratio of 20), and they also provide much better stability than other types of lamp in the ultraviolet and in a portion of the visible.

Other types of lamps could be envisaged. In particular halogen lamps (towards the infrared) or plasma discharge lamps (visible and UV), or plasma sources are particularly suitable, even when they have emission spectrum lines (non-continuous spectrum).

2) Its photomultiplier 5 is placed together with magnetic protection in a low temperature environment, thereby reducing and stabilizing its dark current.

For this purpose, a Peltier effect cooling system is used (−15° C.).

By reducing the dark current of the photomultiplier, noise is reduced by at one least decade (from 200 cps to 10 cps, for example).

Thus, the above-mentioned effects of offset instability are eliminated.

Temperatures that are even lower further improve the performance of the photomultiplier to a few counts per second.

In a spectral range such as the ultraviolet, when using a $D_2$ lamp, source emission noise is low. DNL is then of the same order of magnitude as the SNL limit. This amounts to saying that the number of dark current counts $N_d$ continues to be negligible, and the signal is degraded solely by a low level of residual source noise $N_{ph}$ (number of photons due to source emission). Because of the intrinsic dark current of the photomultiplier is reduced, precise ellipsometic measurement is obtained, which is not possible when $N_{ph} \leqq N_d$.

This reduction in dark current makes it possible in particular to perform measurements at 187 nm, with a low power lamp and in an environment that is not restricted (no vacuum, no purging with an inert gas, no dry atmosphere). The photomultiplier operates in a photon counting mode and ideally it is linear (no non-linearity associated with avalanche overlap effects (saturation in analog mode)).

This limit of 160 nm can also be crossed by using inert gas conditions (nitrogen) with a PMT (R7639 from Hamamatsu) and a corresponding monochromator. In the extreme ultraviolet (120 nm to 160 nm), it is advantageous to cool the base of the photomultiplier 5, or to perform $N_2$ sweeping in the photomultiplier enclosure cooled by a cooler element of the Peltier heat exchanger type, thus avoiding the need for a $MgF_2$ window.

3) Furthermore, the proposed spectroscopic ellipsometer counts over a large number of channels: up to more than 1024 channels, which combined with Fourier analysis oversamples the signal and provides effective filtering of high frequency noise components, i.e. of intrinsic noise from the sources and the detector and the electronics.

The time required for counting is reduced.

This counting technique turns out to be much better than that which is possible using the Hadamard method. It can be implemented very simply by using commercially available electronics. The oversampling it provides contributes to attenuating noise at all of the high frequencies associated with lamp noise.

Detailed Example of One Possible Embodiment

Figure 2:
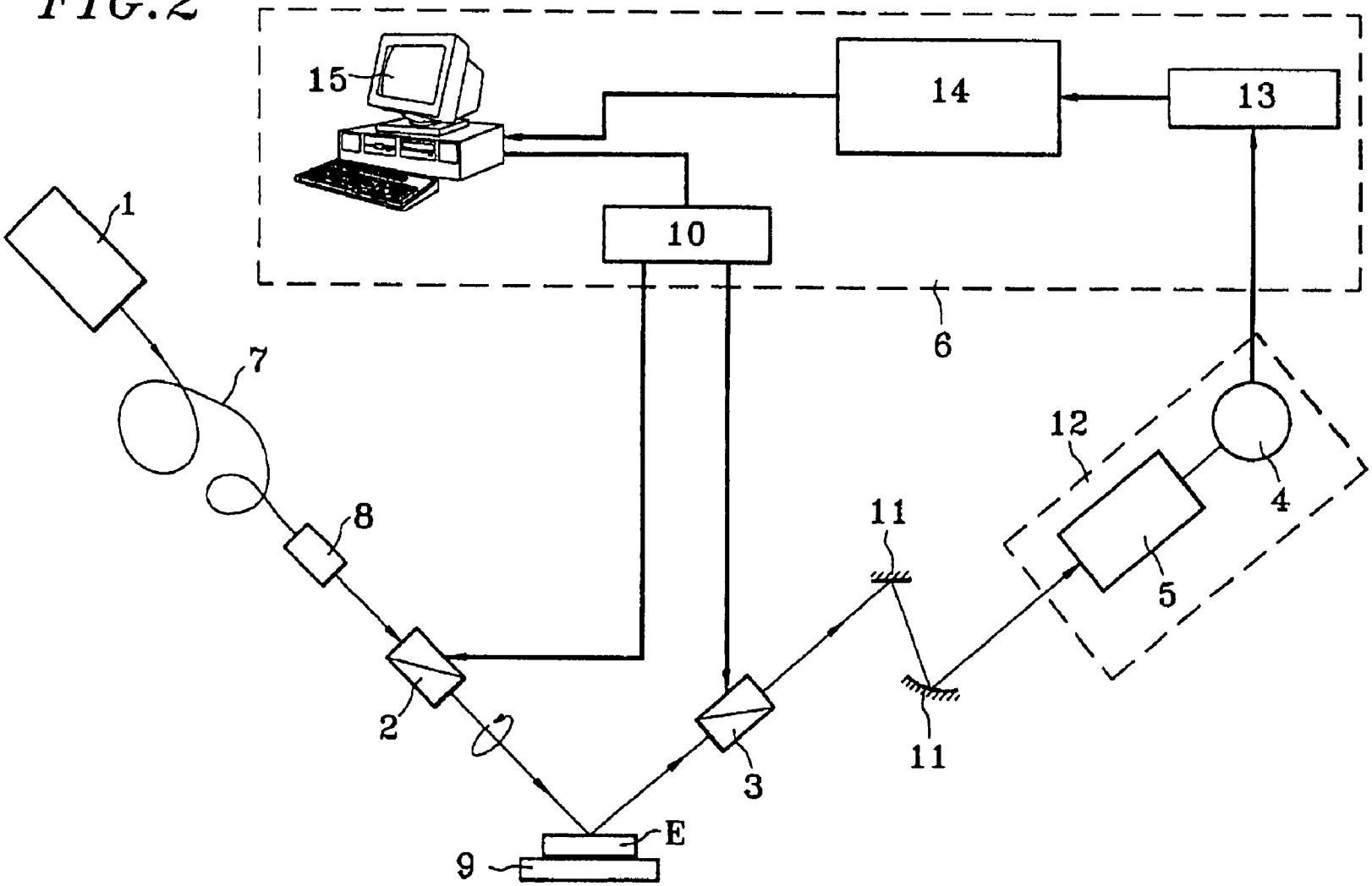
FIG. 2 is a block diagram of an ellipsometer constituting an embodiment of the invention.

An example of an ellipsometer constituting a possible embodiment is described below in detailed manner with reference to FIG. 2.

This ellipsometer is of the type having a rotary polarizer.

It operates in the range 180 nm to 750 nm. It can be used in a vacuum or in a controlled atmosphere so as to extend its operating range to the range 130 nm to 720 nm.

The source 1 is a deuterium lamp ($D_2$) having power of 30 W and a point source diameter of 0.5 millimeters (mm) (Oriel 63163 lamp or Hamamatsu L7295 or L7296 lamp).

The light beam is transferred from the source 1 by means of a 600 μm single strand fused silica fiber 7 to the rotary polarizer 2. One of the functions of the fiber is specifically to eliminate the residual birefringence of the source 1.

Coupling with the rotary polarizer 2 is performed via a converging element 8 of fused silica, selected for its low residual birefringence and its transparency in the ultraviolet.

It can also be implemented using an assembly comprising a concave mirror and a plane mirror, both having $MgF_2$ surface treatment.

The sample E for analysis is placed at the outlet from the polarizer 2 on a support 9 whose orientation can be adjusted.

The beam reflected by the sample is applied to the analyzer 3.

Both the polarizer 2 and the analyzer 3 are made of $MgF_2$ (for example they are constituted by analyzers and polarizers from Fichou/Optique which certifies 2.5° of deviation at 250 nm and a passband to 10 electron volts (eV)). This choice of material makes it possible to obtain greater transparency in the ultraviolet.

The polarizer 2 is rotated at a frequency of about 10 Hz (with the criteria for selection being associated with the environment, mains frequency or vibration frequency) and is controlled by a mechanical assembly of the stepper type (microstep).

After being reflected on the sample and passing through the analyzer 3, the beam is refocused by a set of mirrors 11 and is applied to the inlet of the monochromator 5 which is a dual monochromator having an Oriel 77250 type ⅛ M grating blazed at 250 nm with 1200 lines (180 nm to 500 nm in first order and an intermediate 0.6 mm slot; its resolution at 500 nm is 4 nm). Gratings blazed at 200 nm but with 600 lines per millimeter (mm) can be used.

While performing a measurement, the system automatically incorporates two filters in succession so as to eliminate higher diffraction orders from the gratings of the monochromator. Control is performed by means of an Oriel filter passer and an Ni DAQ (TTL) interface from National Instrument.

The output from the monochromator 5 is applied to the detector 4 which serves to count photons. The detector 4 is of the tube type and it is sold by Hamatsu under the reference R2949 or R7639.

The detector 4 is placed in a cooler 12 of the C-659S type which maintains it at a temperature of −15° C.

The counting electronics includes a discriminator 13 connected to the detector 4. The discriminator is of the type sold by Hamatsu under the reference C 3866 and it has a linear dynamic range of $10^7$.

The detector 4 and the discriminator 13 are selected for their low dark current characteristics (159 cps at 25° C. and dropping to less than 10 cps when cooled for the R2949 and to less than 1 cps for the R7639 (which has quantum efficiency of 44% at 160 nm)). This can be implemented using water cooling or "cryogenic" nitrogen flow cooling with external cooling being provided by Peltier cooling elements and an external heat exchanger. The detector and the discriminator are also selected for their sensitivity in the blue of 8.3 μA/1 m with gain of $10^7$. The photon counting electronics is linear for $10^7$ photons.

The TTL output from the discriminator 13 is analyzed by means of a multiscale count card 14 (MCS II Nuclear Instrument or FMS Canberra Electronics card CM 7882) capable of analyzing 8192 count channels, with two simultaneous inputs and a sampling time of 2 μs.

The card 14 is controlled by a computer 15 operating in a Windows NT server environment with object C++ programming coupled with commercial active X components, in this case the Works++ components from National Instruments.

Example of Results

Figure 3A:
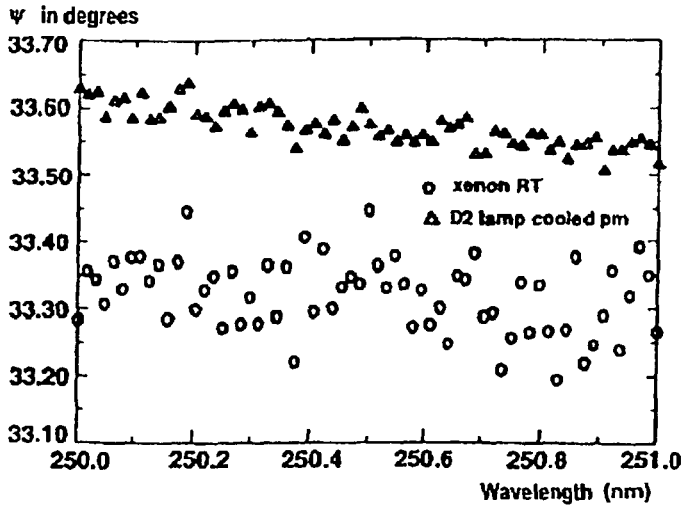
FIGS. 3a and 3b are graphs on which measurements of the parameters Ψ and Δ are plotted as a function of wavelength for an ellipsometer as shown in FIG. 2 and for a standard ellipsometer.
Figure 3B:
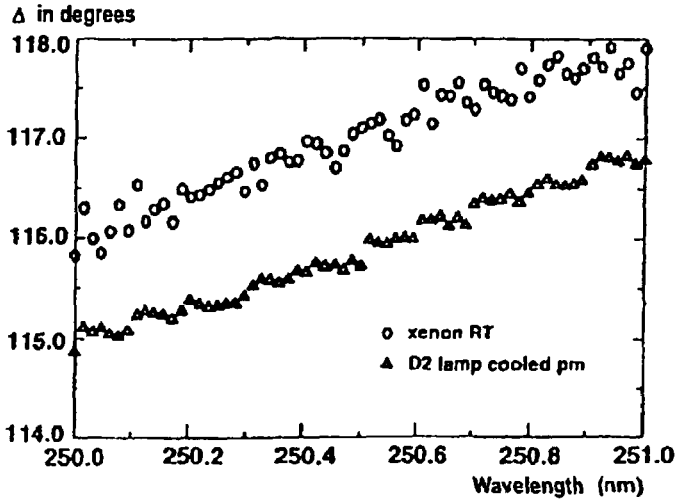

FIGS. 3a and 3b show measurements of Ψ and Δ obtained over a wavelength range of 1 nanometer (around 250 nm) respectively when using a standard xenon lamp ellipsometer, photomultiplier at ambient temperature and Hadamart detection, and when using an ellipsometer as described above.

It can be seen that measurements are much more widely dispersed with the standard ellipsometer than with an ellipsometer of the type described above.

Direct traces obtained with each of the two ellipsometers have also been compared.

Figure 4:
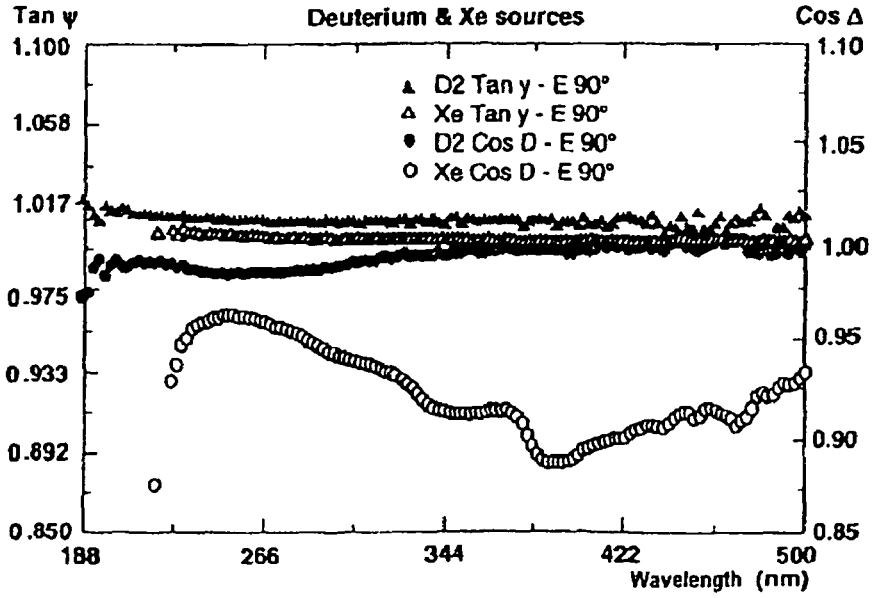
FIG. 4 is a graph showing direct trace measurements obtained by an ellipsometer as shown in FIG. 2 and by a standard ellipsometer, the measurements being plotted as a function of wavelength.

This is shown in FIG. 4.

The improvement is also clearly visible.

It is recalled that for a direct trace, it is necessary that $\tan \omega = \cos \Delta = 1$.

This turns out to be exactly true (ignoring optical alignment) for the above-described low noise spectroscopic ellipsometer, whereas with a standard ellipsometer, the difference is much larger for $\cos \Delta$ which means that it is then important to normalize α and β.

One application consists in extending an in situ setup. The rotary polarizer system and the analyzer are $MgF_2$ lumps mounted in a vacuum on stepper micromotors (vacuum technology) having a hollow shaft (in which the $MgF_2$ lump is inserted) and the optical encoder which can thus be positioned even inside a casing or a cooling and measurement chamber of a cluster tool type reactor. The source and analysis inputs are then compact blocks. This makes it possible to implement two heads (analyzer and polarizer being equivalent). An estimate of the physical size that can be achieved corresponds to a cylinder having a diameter of about 40 mm and a length of 60 mm to 70 mm. Windows which are sources of birefringence and of absorption are thus eliminated since only the optical fibers are connected to the casing of the reactor. It has been shown that such a system can operate in situ for photons having wavelengths in the spectrum range 160 nm to 170 nm.

What is claimed is:

1. A spectroscopic ellipsometer comprising a light source [(1)] emitting a light beam, a polarizer [(2)] placed on the path of the light beam emitted by the light source, a sample support [(9)] receiving the light beam output from the polarizer, a polarization analyzer [(3)] for passing the beam reflected by the sample to be analyzed, a detection assembly which receives the beam from the analyzer and which comprises a monochromator [(5)] and a photodetector [(4)], and signal processor means [(6)] for processing the signal output from said detection assembly, and including counting electronics [(13)], the ellipsometer being characterized in that it further comprises cooling means [(12)] for keeping the detection assembly at a temperature lower than ambient temperature.

2. An ellipsometer according to claim 1, characterized in that said cooling means [(12)] are suitable for keeping the detection assembly at a temperature of about −15° C. or lower.

3. An ellipsometer according to claim 1, characterized in that the source [(1)] is constituted by a deuterium lamp.

4. An ellipsometer according to claim 3, characterized in that the lamp has power of about 30 watts.

5. An ellipsometer according to claim 1 or claim 2, characterized in that the source is constituted by a cold plasma lamp.

6. An ellipsometer according to claim 1 or claim 2, characterized in that the source is constituted by a halogen lamp.

7. An ellipsometer according to claim 1, characterized in that the counting electronics [(13)] is suitable for performing amplitude sampling over a number of channels equal to about 1000 or more.

8. An ellipsometer according to claim 6, characterized in that the counting electronics [(13)] is suitable for implementing amplitude sampling over a number of channels lying in the range 1024 to 8192.

9. An ellipsometer according to claim 7 or claim 8, characterized in that the processor means [(6)] apply Fourier analysis to the signal output by the counting electronics.

*10. A spectroscopic ellipsometer comprising:*

*a light source configured to emit a light beam,*

*a polarizer placed on the path of the light beam emitted by the light source,*

*a sample support configured to support a sample such that the sample is arranged to receive the light beam output from the polarizer,*

*a polarization analyzer arranged to allow passage of the light beam reflected by the sample,*

*a detection assembly including a monochromator arranged to receive the light beam from the analyzer and a photodetector arranged to receive an output from the monochromator, and*

*a signal processor configured to process a signal output from said detection assembly,*

*wherein the ellipsometer further comprises a cooling apparatus configured to maintain the monochromator and the photodetector at a temperature lower than ambient temperature.*

*11. The ellipsometer as recited in claim 10, wherein said cooling apparatus is configured to maintain the detection assembly at a temperature of about −15° C. or lower.*

*12. The ellipsometer as recited in claim 10, wherein the light source is a deuterium lamp.*

*13. The ellipsometer as recited in claim 12, wherein the lamp has power of about 30 watts.*

*14. The ellipsometer as recited in claim 10, wherein the light source is a cold plasma lamp.*

*15. The ellipsometer as recited in claim 10, wherein the light source is a halogen lamp.*

*16. The ellipsometer as recited in claim 10, wherein the signal processor includes counting electronics, and wherein the counting electronics are configured to perform amplitude sampling over a number of channels equal to about 1000 or more.*

*17. The ellipsometer as recited in claim 16, wherein the counting electronics are configured to implement amplitude sampling over a number of channels lying in the range 1024 to 8192.*

*18. The ellipsometer as recited in claim 16, wherein the signal processor is configured to apply Fourier analysis to a signal output by the counting electronics.*

*19. An ellipsometer comprising:*

*a detection assembly including a monochromator arranged to receive a beam of light and a photodetector arranged to receive an output from the monochromator and configured to count photons in the output received from the monochromator;*

*a cooling apparatus, wherein the cooling apparatus is configured to maintain the detection assembly at a temperature lower than ambient temperature.*

*20. The ellipsometer as recited in claim 19, wherein the cooling apparatus is configured to maintain the detection assembly at a temperature of approximately −15° C. or lower.*

*21. The ellipsometer as recited in claim 19, further comprising a light source configured to emit the beam of light.*

*22. The ellipsometer as recited in claim 21, further comprising a polarizer configured to polarize the beam of light.*

*23. The ellipsometer as recited in claim 22, wherein the polarized beam of light is reflected from a sample material through a polarization analyzer to be received by said detection assembly.*

*24. The ellipsometer as recited in claim 23, wherein said ellipsometer further comprises a pair of mirrors arranged to focus the beam of light to be received by said detection assembly to an inlet of the monochromator.*

*25. The ellipsometer as recited in claim 24, wherein the photodetector is configured to count photons.*

*26. A method of reducing detector noise in an ellipsometer, the method comprising:*

*cooling a detection assembly within the ellipsometer so as to maintain the detection assembly at a temperature lower than ambient temperature, the detection assembly including a monochromator and a photodetector coupled to receive an output from the monochromator; and*

*analyzing optical properties of a sample material using an output signal of the detection assembly of the ellipsometer.*

*27. The method as recited in claim 26 further comprising maintaining the detection assembly at or below a predetermined temperature.*

*28. The method as recited in claim 27, wherein the predetermined temperature is −15° C.*

*29. The method as recited in claim 26, further comprising:*

*projecting a beam of light from a light source;*

*reflecting the projected beam of light off the sample material;*

*the monochromator receiving the reflected beam of light.*

*30. The method as recited in claim 29, further comprising polarizing the beam of light prior to said reflecting.*

*31. The method as recited in claim 30, further comprising using mirrors to focus the reflected beam of light prior to said receiving.*

* * * * *

UNITED STATES PATENT AND TRADEMARK OFFICE

CERTIFICATE OF CORRECTION

PATENT NO. : RE44,007 E
APPLICATION NO. : 11/520061
DATED : February 19, 2013
INVENTOR(S) : Ferrieu It is certified that error appears in the above-identified patent and that said Letters Patent is hereby corrected as shown below:

On the title page, item (56), under "FOREIGN PATENT DOCUMENTS", in Column 2, Line 2, delete "DE 29521772 9/1998".

On title page 2, item (56), under "FOREIGN PATENT DOCUMENTS", in Column 1, Line 7, delete "JP 9079905 3/1997".

On title page 2, item (56), under "FOREIGN PATENT DOCUMENTS", in Column 1, Line 8, delete "JP 09079905 7/1997".

In the Specification

In Column 2, Line 38, delete "Hadamart" and insert -- Hadamard --, therefor.

In Column 2, Line 41, delete "Ω," and insert -- ω, --, therefor.

In Column 2, Line 42, delete "2Ω" and insert -- 2ω --, therefor.

In Column 3, Line 19, delete "light is source," and insert -- light source, --, therefor.

In Column 3, Line 46, delete "and a" and insert -- and iii) a --, therefor.

In Column 6, Line 3, delete "Hamatsu" and insert -- Hamamatsu --, therefor.

In Column 6, Line 9, delete "Hamatsu" and insert -- Hamamatsu --, therefor.

In Column 6, Line 38, delete "Hadamart" and insert -- Hadamard --, therefor.

In Column 6, Lines 47-48, delete "tanω=CosΔ=1." and insert -- tanψ=CosΔ=1. --, therefor.

In the Claims

In Column 8, Line 51, in Claim 27, delete "26" and insert -- 26, --, therefor.

Signed and Sealed this
Twentieth Day of May, 2014

Michelle K. Lee

Michelle K. Lee
*Deputy Director of the United States Patent and Trademark Office*